United States Patent [19]

Giebeler, Jr.

[11] Patent Number: 4,622,972
[45] Date of Patent: Nov. 18, 1986

[54] ULTRASOUND HYPERTHERMIA APPLICATOR WITH VARIABLE COHERENCE BY MULTI-SPIRAL FOCUSING

[75] Inventor: Robert H. Giebeler, Jr., Sunnyvale, Calif.

[73] Assignee: Varian Associates, Inc., Palo Alto, Calif.

[21] Appl. No.: 418,136

[22] Filed: Sep. 15, 1982

Related U.S. Application Data

[63] Continuation-in-part of Ser. No. 308,924, Oct. 5, 1981, abandoned.

[51] Int. Cl.⁴ .................................................. A61F 7/00
[52] U.S. Cl. ................................ 128/399; 128/24 A; 367/138
[58] Field of Search ................ 128/24 A, 303 R, 399, 128/804, 660; 73/625, 641; 310/335; 367/138

[56] References Cited

U.S. PATENT DOCUMENTS

| | | | |
|---|---|---|---|
| 2,968,302 | 1/1961 | Fry et al. | 128/24 A |
| 3,237,623 | 3/1966 | Gordon | 128/24 A |
| 3,958,559 | 5/1976 | Glenn et al. | 128/24 A X |
| 4,070,905 | 1/1978 | Kossoff | 73/641 |
| 4,440,025 | 4/1984 | Hayakawa | 128/660 |
| 4,441,486 | 4/1984 | Pounds | 128/24 A |

OTHER PUBLICATIONS

Marmor et al, "Treating Spontaneous Tumors . . . ", Int. J. Rad. Onc. Biol. Phys., vol. 4, pp. 967–973, 1978.
Rivin et al, "Ultrasonic Hyperthermia System . . . ", Med. Inst., vol. 14, No. 6, pp. 325–328, Nov., Dec. 1980.
Lele, "Induction of Deep, Local Hyperthermia . . . ", Radiat. Environ. Biophys., 17, 205–217, 1980.
Lele, "An Annular Focus Ultrasonic Lens . . . ", Ultrasound Med. & Biol., 7, 191–193, 1981.
Beard et al, "An Annular Focus Ultrasonic Lens . . . ", Ultrasound in Med. & Biol., vol. 8, No. 2, pp. 177–184, 1982.

*Primary Examiner*—Lee S. Cohen
*Attorney, Agent, or Firm*—Stanley Z. Cole; John Yakes; Peter J. Sgarbossa

[57] ABSTRACT

An ultrasound hyperthermia applicator comprises a plurality of transducers which can be operated in different grouping modes so that the applicator is effectively provided with a variable number of elements having variable effective diameters transmitting coherent beams. The individually coherent beams from these elements are individually focused for incoherent superposition in the target volume according to a spiral or multi-spiral focusing scheme. Such an applicator is capable of uniformly heating without scanning a limited part of human body with volume greater than the inherent focal size of the individual transmitter element.

60 Claims, 6 Drawing Figures

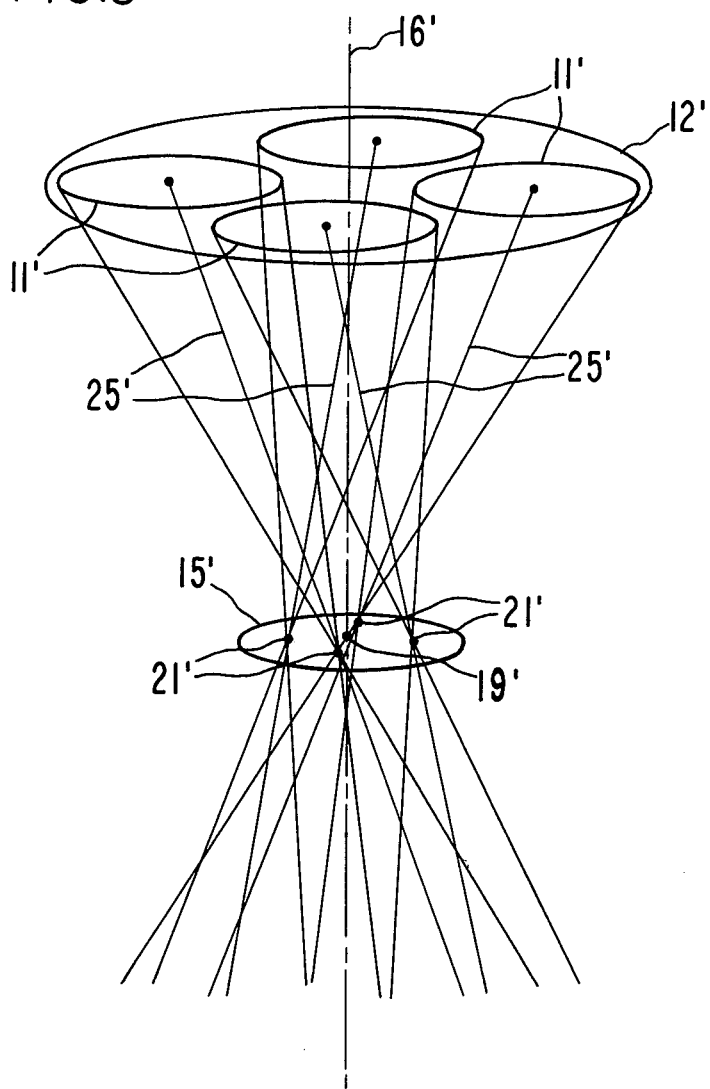

ULTRASOUND HYPERTHERMIA APPLICATOR WITH VARIABLE COHERENCE BY MULTI-SPIRAL FOCUSING

This is a continuation-in-part of application Ser. No. 308,924 filed Oct. 5, 1981, now abandoned.

BACKGROUND OF THE INVENTION

This invention relates to an apparatus for heating limited parts of a human body and more particularly to an ultrasound hyperthermia applicator capable of uniformly heating relatively large volumes locally without scanning.

Hyperthermia is a name which has come to mean high temperature in humans induced with therapeutic intent. Its application to cancer therapy is based on the discovery that malignant cells are generally more sensitive to heat than are normal cells. Physical techniques for hyperthermia include metabolic heat containment, heating by radio frequency or microwave energy absorption, conduction through the skin such as by a hot water bath, and perfusion of externally heated blood, heated intravenous fluids and anesthetic gases, but ultrasound is well known to offer advantages in that it has good penetration in tissue and that ultrasound heating can be focused and localized. The latter characteristic is particularly important because serious damage to healthy tissue and skin in the surrounding region must be avoided. For a given fixed frequency of ultrasound, however, the focal volume size for a single coherent focused transducer cannot be changed so that the treatment of a volume larger than the inherent focal size has previously been done by scanning, but scanning results in a high peak to average power ratio, and also introduces the complex problem of rapidly and accurately scanning the region to be heated.

SUMMARY OF THE INVENTION

It is therefore an object of the present invention to provide an apparatus for heating a tissue volume deep within a patient without the necessity of scanning.

It is another object of the present invention to provide an ultrasound hyperthermia applicator capable of generating a variety of heating patterns by selection of frequency and the effective diameter and focal length of the individual coherent transmitter elements.

BRIEF DESCRIPTION OF THE DRAWINGS

FIG. 3 shows schematically the spiral focusing method embodying the present invention according to which an incoherent superposition of individually coherent beams individually focused on a target plane does not result in any undesired points of increased heat intensity outside the target volume.

DETAILED DESCRIPTION OF THE INVENTION

Figure 1:
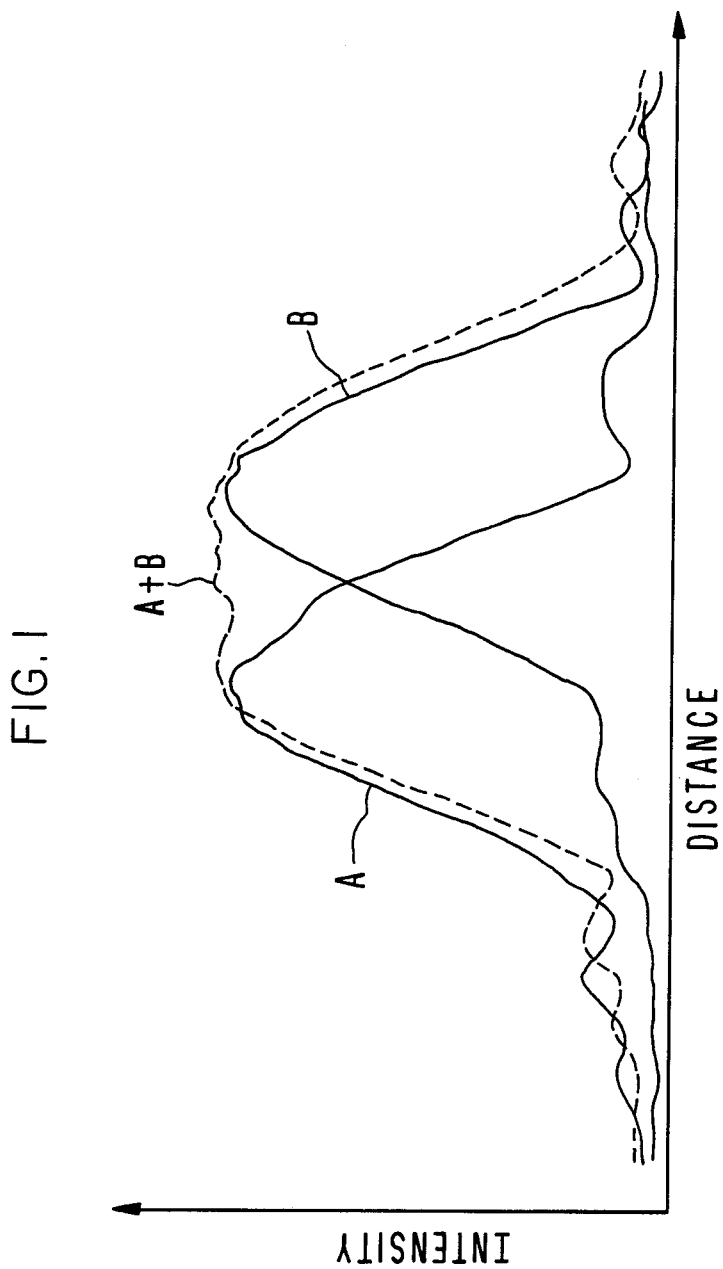
FIG. 1 shows qualitatively how an incoherent superposition of two individually coherent and individually focused beams can produce the effect of uniformily heating an extended region.
Figure 2:
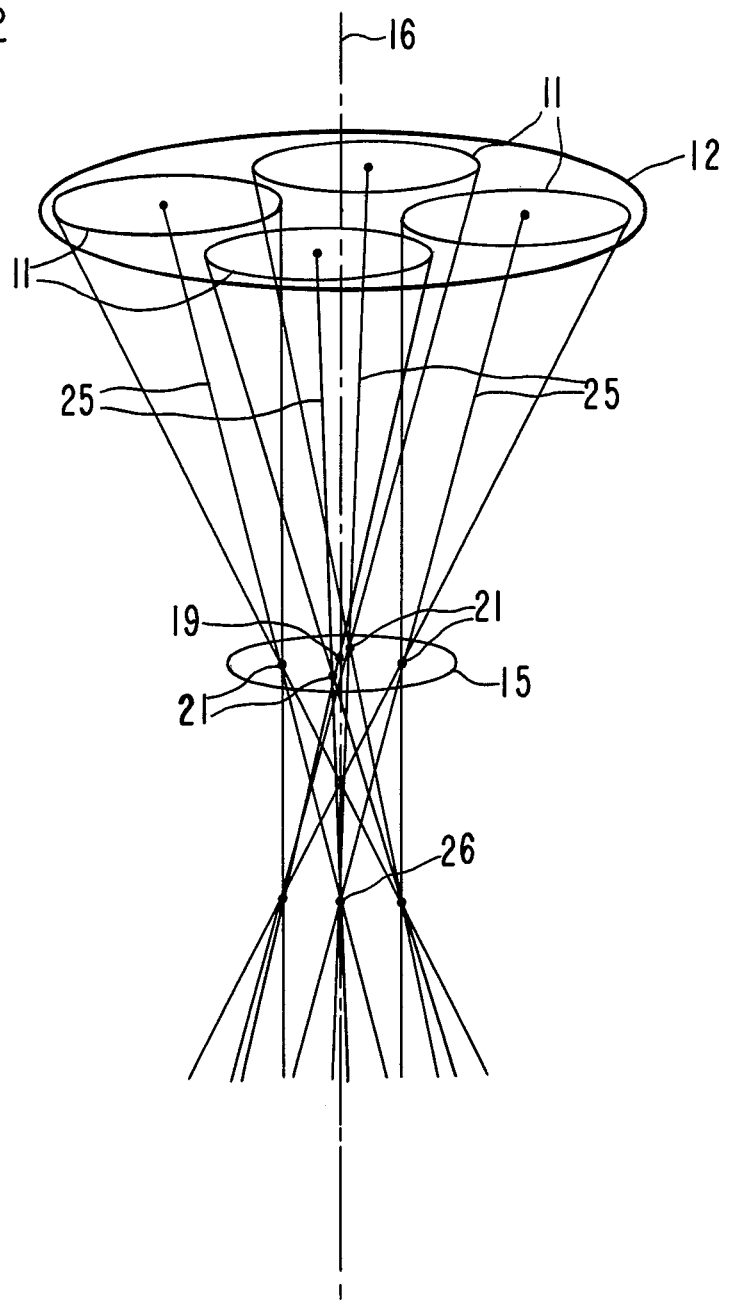
FIG. 2 shows schematically how an incoherent array of individually coherent beams individually focused on a target plane can have a point of maximum heat intensity some distance away from the target plane.

Stated briefly, the basic principle upon which the present invention relies is that uniform heating becomes possible by incoherent superposition of two coherent ultrasound beams in the far field. Any coherent ultrasound beam in the far field has a transverse intensity profile as shown by Curve A of FIG. 1. If another such coherent beam shown by Curve B is incoherently superposed, the resultant profile is shown by Curve (A+B) which rises and falls as rapidly as Curves A and B, but remains relatively constant over an extended distance. Thus, it is theoretically possible to obtain almost any resultant pattern of power level by superposition of many incoherent beams in this manner. This must be done, however, so that their beam center lines will not intersect outside the treatment volume because such intersection point will represent a position of maximum heat intensity. Referring now to FIG. 2 which schematically shows a typical example whereby such point of maximum intensity occurs outside the treatment volume, four transmitter elements 11, each having a finite effective beam diameter shown by a circle, are placed in an approximately square formation on transducer plane 12 some distance away from and directly facing the target area 15, that is, the line 16 through the center of the square formation and normal to transducer plane 12 will also pass through the center 19 of and is perpendicular to the plane of target area 15. Four focal points 21 are selected on target area 15 in an approximately square formation so that they are not only at a same distance from line 16, but also at the same azimuthal angles with respect to line 16 as the transmitter elements 11.

Each of the transmitter elements 11 is a source of coherent beams and is focused at the nearest of the focal points 21, or that focal point which is at the same azithumal angle as the transmitter element itself with respect to line 16. This focusing scheme is illustrated in FIG. 2 by means of representative beams from each element 11 including beam center line 25. The four transmitter elements 11 are focused incoherently with respect to one another, but this scheme for incoherent superposition of individually coherent beams is not satisfactory because the four beam center lines 25 intersect one another on line 16 at point 26. This will turn out to be a point of maximum heat intensity and it is likely that this point may lie outside the target volume.

The present invention is addressed to the problem of eliminating this difficulty. Referring now to FIG. 3 illustrating the spiral focusing scheme of the present invention by a simple example, components corresponding to those of FIG. 2 are given like reference numerals. Four transmitter elements 11' are positioned opposite to, and four focal points 21' are selected on target area 15' in an identical manner as in FIG. 2, but each of the transmitter elements 11' is focused not on the nearest of the focal points 21' (i.e., the one at the same azimuthal angle with respect to the center line 16' as the transmitter element), but on the one displaced therefrom by 90° counterclockwise (seen from above). As a result, the four beam center lines 25' are now in a spiral-like formation and hence are prevented from intersecting one another. In fact, FIG. 3 indicates that the position of maximum intensity is spread over the target area itself.

Figure 4A:
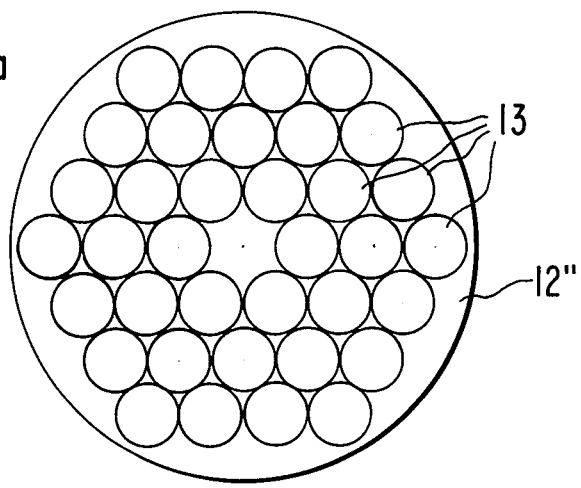
FIGS. 4a, 4b and 4c show examples of how individual transducers can be arranged on a plane so that they can be driven according to various grouping schemes.
Figure 4B:
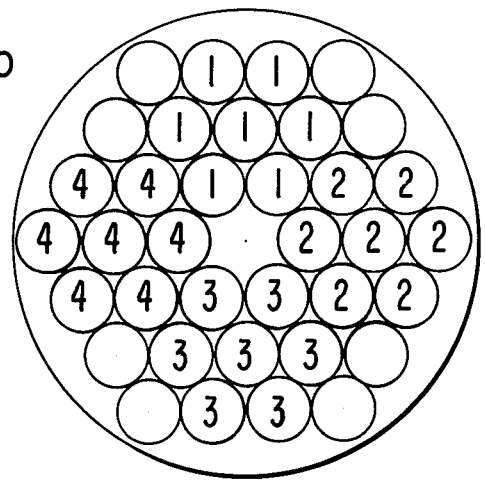
Figure 4C:
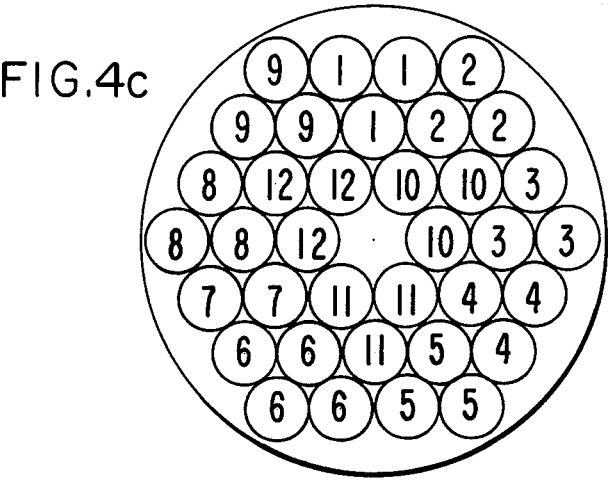

As one of the preferred embodiments of the present invention based on the principle described above, FIG. 4(a) shows 36 transducer elements 13 which are brazed to base plate 12" into a regular hexagonal shape in such a way that the lines connecting the centers of the mutually adjacent circles, each representing the effective diameter of the beams from a transducer element, form a closely packed matrix of equilateral triangles. RF power at fundamental or high resonant mode frequencies, dependent on the depths of treatment, can be matched to each transducer element via a multitrap toroidal impedance transformer (not shown). Each of elements 13 may be individually focused, or alternatively a group of several adjacent transducers can be made to act as a coherent transmitter element of a larger effective diameter. In FIGS. 4(a) and (c), two such examples are shown wherein transducers marked by the same numeral are to form a single transmitting element (e.g., 11 of FIG. 2) while transducers marked by differential numerals are emitters of beams for incoherent superposition. FIG. 4(b) shows a mode in which 8 of the 36 available transducers are not activated and the remaining transducers are divided into 4 groups (transmitting elements) of 7 (transducers) each, approximating the situation shown in FIG. 3. FIG. 4(c) shows another example of grouping whereby the 36 transducers are divided into 12 groups (transmitting elements) of 3 (transducers) each.

The beams from each transmitter element thus formed by a single transducer (as in FIG. 4(a)) or a group of transducers (as in FIGS. 4(b) and (c)), are focused at a selected target point according to a scheme as illustrated in FIG. 3.

According to the spiral focusing scheme which embodies the present invention, a target area (like 15' of FIG. 3) with a finite effective diameter is selected and the base plate 12" is positioned directly opposite to it some distance away so that a central line normal to both the base plate and the target area is definable (as line 16' of FIG. 3). Beams from each transmitter element are focused at a particular target point on the target plane in such a way that (1) these target points describe on the target plane a pattern which is similar (in the sense of the word used in geometry), but rotated around the central normal line by a fixed angle with respect to the pattern formed on the plane of base plate by the centers of the effective beam diameters of the transmitter elements and that (2) each beam center line (like 25' of FIG. 3) connects corresponding points of the two similar patterns. Stated in another way, beams from a transmitter element whose center is at distance R from and at azimuthal angle A (with respect to a fixed reference direction) around the central normal line defined above are focused on the target plane at a point at distance rR from and at azimuthal angle A+Z where r is a predetermined multiplicative factor less than unity and Z is a fixed angle (of spiral rotation).

As a result of the focusing scheme described above, the beam center lines assume a spiral-like formation around the central normal line as shown in FIG. 3. If a large number of transmitter elements are used so that their distances to the central normal lines are not uniform, the beam center lines may assume a double or multi-spiral formation. The preferred angle of rotation also changes according to the distribution of the transmitter element because it should not be so small that points of substantially enhanced heating may appear outside the target volume, while it should not be so large that beams from adjacent transmitter elements may intersect each other. In the case of four transmitter elements installed in a substantially square formation as shown in FIGS. 2, 3 or 4(b), the angle of spiral rotation (i.e., mZ) should be in the range of about 30°–150° and preferably nearly equal to 90°.

Focusing of the beams from individual elements according to any of the above-described schemes is accomplished by placing an acoustic lens (not shown) parallel to the transducer plane 12 and in front of the transducers 11. The lens is easily removable and exchangeable with another of different type so that different focusing characteristics can be obtained. A patient interface (not shown), or the surface through which the applicator may come into contact with the patient, is made of thin rubber. In order to prevent overheating of the applicator components such as the transducers, the acoustic lens and the patient interface, a system of passages (not shown) is provided for circulating a liquid such as water. The liquid can circulate both through passages between the lens and the transducers and those between the front surfaces (facing the patient) of the lens and the patient interface for efficient cooling.

The present invention has been described above in terms of only a few particular embodiments. The above description, however, is to be considered as illustrative rather than limiting. For example, the beams need not be ultrasound waves. The technique of the present invention is equally applicable to apparatus using transverse waves such as microwaves and infrared, optical or ultraviolet waves. The total number of transducers to be affixed to the base plate can be varied freely. Since the basic principle is to employ an incoherent array of individually coherent and individually focused beams, any number of such individual sources of coherent beam can be used in an applicator of the present invention. They may be affixed to their predetermined positioned by any method. Any number of individual transducers may be grouped together to form a transmitter element of the type shown in FIG. 3 (not necessarily 7 as in FIG. 4(b) or 3 as in FIG. 4(c)), and hence the size and pattern of such elements can also be varied. Any method known in the arts may be used to drive transducers within each transmitter element to emit coherent beams. The pattern according to which the centers of transmitter elements are distributed on the transducer plane need not be exactly identical to that of their foci as long as the plane of maximum heat intensity is formed substantially close to the plane of their foci for the purpose of treatment. Focusing of the beams and cooling of the device can be accomplished by any method. Passages for circulating a liquid may be provided according to any reasonable design. The scope of the invention is limited only by the following claims.

What is claimed is:

1. A device for uniformly irradiating a target volume by an array of individually focused beams without forming outside said target volume a hot spot, said device comprising a plurality of beam transmitter elements having finite effective beam diameters and positioned at predetermined source locations about a central axis of the device, each of said transmitter elements defining a straight beam center line and transmitting beams which are focused on said beam center line and at one of a plurality of preselected target points distributed within said volume, said beam center lines being in a mutually non-intersecting relationship, said beam center lines approaching closer to said central axis with distance toward said target volume.

2. The device of claim 1 wherein said beams are ultrasound beams and each of said transmitter elements comprises one or more transducers.

3. A device as in claim 2 in which said array is an incoherent array of said individually coherent beams.

4. The device of claim 1 wherein all said source locations lie on a transmitter plane and said target points lie on a target plane which is parallel to said transmitter plane.

5. The device of claim 1 wherein said beam transmitter elements comprise a plurality of transducers which can be operated to transmit coherent beams both individually and in groups.

6. The device of claim 5 wherein each of said transducers has an inherent focal volume size associated with itself, said target volume being larger than said inherent focal volume size of each of said transducers.

7. The device of claim 5 wherein the number of said transmitter elements and said effective diameters are variable by operating said transducers in different grouping modes.

8. A device as in claim 1 in which said straight beam center lines diverge from said device central axis beyond said target volume.

9. A device as in claim 1 in which said target points each correspond respectively to one of said source locations, said target points being rotated about said central axis with respect to corresponding ones of said source locations.

10. A device as in claim 1 in which said beams are individually coherent.

11. A device as in claim 1 in which said beam center lines and said device central axis are in a mutually non-intersecting relationship.

12. A device for uniformly irradiating a target volume by an incoherent array of individually coherent and individually focused beams without forming outside said target volume a hot spot, said device comprising a plurality of beam transmitter elements having finite effective beam diameters and positioned at predetermined source locations, said source locations lying on a transmitter plane, each of said transmitter elements defining a beam center line and transmitting coherent beams which are generally in the direction of said beam center line and are focused on said beam center line and at one of a plurality of preselected target points distributed within said volume, said target points lying on a target plane which is parallel to said transmitter plane, said beam center lines being in a mutually non-intersecting relationship, the geometrical pattern of said source locations on said transmitter plane being similar to the pattern of said target points on said target plane, said pattern of source locations being in a rotated relationship with said pattern of target points around an axis perpendicular to said transmitter plane by a predetermined angle.

13. The device of claim 12 wherein said angle is in the range of 30° to 150°.

14. A method of uniformly irradiating without scanning a target volume by an incoherent array of individually coherent beams which are individually focused, said method comprising the steps of selecting a number of target points distributed inside said volume about a central axis, positioning a plurality of beam sources having finite effective diameters at source locations about said central axis, each of said beam sources being adapted to define a beam center line and to transmit coherent beams which are generally in the direction of said beam center line and are focused on said beam center line, and irradiating said target volume with said beam sources, each of said beam sources being focused at one of said target points and said beam center lines being positioned in a mutually non-intersecting relationship whereby undesirable heating does not occur outside said target volume, said target points defining a pattern which is rotationally displaced about said central axis relative to the pattern about said axis which is defined by the centers of said sources.

15. The method of claim 14 wherein said pattern of target points is rotationally displaced relative to said pattern defined by said centers of said sources by an angle in range 30°–150°.

16. A device for irradiating a target volume comprising a plurality of energy sources distributed around a center axis of the device, each of said energy sources transmitting a beam having a center line intersecting said target volume, said center lines being directed toward but not at the device center axis between said sources and said target volume.

17. The device of claim 16 wherein each of said energy sources is a compressional wave source.

18. The device of claim 16 wherein the sources are radially positioned around the device center axis.

19. The device of claim 16 wherein the beams are focused.

20. A device as in claim 16 in which said center lines approach said device center axis over the distance between said sources and said target volume, and diverge from said device center axis beyond said target volume.

21. A device as in claim 16 in which the intersection of each said center line with the target volume in a plane orthogonal to the device axis is rotated about said device axis relative to the original position of said center line at its corresponding source.

22. A device as in claim 16 in which the distance, measured orthogonally to the device center axis, between said axis and said center line at the target volume is less than the distance between said center line and said axis at the source corresponding to said center line.

23. A device as in claim 16 in which the distance measured orthogonally to the device center axis between said axis and said center line at the target volume is less than the distance between said center line and said axis at locations on said center line downstream of said target volume.

24. A method of irradiating target regions located inside a target volume comprising deriving wave energy from wave energy source means located at a plurality of locations displaced from the regions and from a longitudinal axis that intersects the target volume, the wave energy being derived from each location as a beam having a center line intersecting the target and directed toward but not at the axis, the beam center lines being positioned so that the center lines do not intersect with each other and do not intersect with the axis.

25. The method of claim 24 wherein energies in different ones of the beams overlap in the target regions.

26. The method of claim 25 further comprising the step of focusing each beam on a different one of the target regions.

27. The method of claim 25 wherein each beam is coherently transmitted at a single frequency.

28. The method of claim 27 wherein the frequencies for the different beams differ from each other.

29. The method of claim 24 further comprising the step of focusing each beam on a different one of the target regions.

30. The method of claim 24 wherein each beam is coherently transmitted at a single frequency.

31. The method of claim 30 wherein the frequencies for the different beams differ from each other.

32. A method of hyperthermia treating diseased tissue in the interior of a treated body without overheating neighboring tissue comprising deriving compressional wave energy from wave energy source means located at a plurality of locations displaced from the diseased tissue and from a longitudinal axis that intersects the body, the wave energy being derived from each location as a beam having a center line intersecting the body and directed toward but not at the axis, the beams center lines being positioned so the center lines do not intersect with each other and do not intersect with the axis.

33. The method of claim 32 wherein the energies in different ones of the beams overlap in the diseased tissue.

34. The method of claim 33 further comprising the step of focusing each beam on a different portion of the diseased tissue.

35. The method of claim 34 wherein each beam is coherently transmitted at a single frequency.

36. The method of claim 35 wherein the frequencies for the different beams differ from each other.

37. The method of claim 32 further comprising the step of focusing each beam on a different portion of the diseased tissue.

38. The method of claim 37 wherein each beam is coherently transmitted at a single frequency.

39. The method of claim 38 wherein the frequencies for the different beams differ from each other.

40. The method of claim 32 wherein each beam is coherently transmitted at a single frequency.

41. The method of claim 40 wherein the frequencies for the different beams differ from each other.

42. The method of claim 32 wherein the center line of each beam is equally displaced from the axis in a common plane at right angles to the axis, and subtends the same angle from the plane and subtends the same angle relative to the longitudinal axis in a second plane that includes the axis and intersects the common plane at right angles.

43. A device for irradiating a target volume comprising a plurality of energy sources distributed around a center axis of the device, each of said energy sources transmitting a beam having a center line directed toward a respective target location within said target volume, said center lines approaching said device center axis over the distance between said sources and said target volume, and diverging from said device center axis beyond said target volume.

44. A device as in claim 43 in which said beam center lines are oriented at an angle to planes containing the center of their respective sources and the device center axis.

45. A device as in claim 43 in which said beam center lines are positioned so that none of them intersect with each other.

46. A device as in claim 43 in which said target locations are rotated about said device center axis relative to the positions of the corresponding sources about said device axis.

47. A device for irradiating a target volume, comprising a plurality of beam source elements positioned at respective source locations about a central axis of the device, each of said elements transmitting a beam directed at one of a plurality of preselected target locations distributed within said volume, said source locations defining a source pattern about said central axis of said device, said target locations defining a target location pattern about said central axis, said target pattern being rotated about said central axis with respect to said source pattern by a predetermined angle.

48. A device as in claim 47 in which each said beam transmitted by each of said beam source elements defines a beam center line, said beam center lines being directed toward but not at said device central axis between said source locations and said target volume, said beam center lines diverging away from said device central axis beyond said target volume.

49. A device as in claim 47 in which each beam defines a beam center line and is focused along this line and on one of said plurality of preselected target location.

50. A device as in claim 47 in which each said beam transmitted by each of said beam source elements defines a beam center line, said beam center lines being in a mutually non-intersecting relationship with each other and with said device central axis.

51. A device as in claim 47 in which said beams are individually coherent.

52. A device as in claim 51 in which said beams are focused on said target locations so as to be incoherently superimposed on said target volume.

53. A device as in claim 47 in which said plurality of beam source elements is provided in at least two arrays, each symmetric about said central axis with the elements of each array at a different distance from said central axis as compared to the elements of the remaining one or more arrays, and with the target locations corresponding to each array rotated at a different said predetermined angle compared to the target locations corresponding to the remaining one or more arrays.

54. A device for irradiating a target volume comprising:
a plurality of beam sources distributed around a center axis of the device,
each of said beam sources transmitting a beam directed toward said target volume, each of said beams defining a beam center line,
each said beam center line being directed to said volume at an angle to a plane defined by said device center axis and the center of said source corresponding to said beam.

55. A device for irradiating a target volume comprising:
a plurality of beam sources distributed around a center axis of the device,
each of said beam sources transmitting a beam directed toward said target volume,
each of said beams being directed to said volume at an angle to the plane defined by said device center axis and the center of said source corresponding to said beam,
each said beam approaching said device center axis at said target volume, but thereafter diverging from said center axis.

56. A device for irradiating a target volume comprising:

a plurality of beam sources distributed around a center axis of the device,
each of said beam sources transmitting a beam directed toward said target volume,
each of said beams being directed to said volume at an angle to the plane defined by said device center axis and the center of said source corresponding to said beam,
the position of each beam's intersection with said target volume being rotated about said device center axis relative to said source of said beam by a predetermined angle.

57. A device for irradiating a target volume comprising:
a plurality of beam sources distributed around a center axis of the device,
each of said beam sources transmitting a beam directed toward said target volume,
each of said beams being directed to said volume at an angle to the plane defined by said device center axis and the center of said source corresponding to said beam,
each of said beams being also directed toward but not at said center axis over the distance between the source corresponding to said beam and said target volume.

58. A device as in any of claims 55, 56, or 57, in which said sources are individually coherent, and their beams are superimposed on said target volume in an incoherent manner.

59. A device for uniformly irradiating a target volume, said device comprising a plurality of beam transmitter elements about a central axis of the device, each element having a finite effective beam envelope and positioned at a respective different predetermined source location, each of said transmitter elements transmitting a beam defining a beam center line and focused at a respective target location, the beam center lines of said transmitter elements not mutually intersecting outside said target volume, the distance between at least one of said beam center lines and said device central axis at the corresponding transmitter element being greater than the distance between said one beam center line and said device central axis at the corresponding target location.

60. A device as in claim 59 in which said beams are individually coherent, and overlap within said target volume in an incoherent manner.

* * * * *